United States Patent [19]

Eifler et al.

[11] 4,025,557

[45] May 24, 1977

[54] PROCESS FOR THE PRODUCTION OF POLYAMINES

[75] Inventors: Willi Eifler, New Martinsville, W. Va.; Hartmut Knöfel, Leverkusen-Schlebusch, Germany

[73] Assignee: Bayer Aktiengesellschaft, Leverkusen, Germany

[22] Filed: Nov. 27, 1974

[21] Appl. No.: 527,551

Related U.S. Application Data

[63] Continuation of Ser. No. 364,187, May 25, 1973, abandoned.

[30] Foreign Application Priority Data

June 3, 1972   Germany ............................ 2227110

[52] U.S. Cl. ............................................ 260/570 D
[51] Int. Cl.² ........................................ C07C 85/145
[58] Field of Search ............................... 260/570 D

[56] References Cited

UNITED STATES PATENTS

| | | | |
|---|---|---|---|
| 1,803,331 | 5/1931 | Kladivko | 260/570 |
| 1,954,484 | 4/1934 | Mattison | 260/570 |
| 3,175,007 | 3/1965 | Berhenke | 260/570 X |
| 3,358,025 | 12/1967 | Foster et al. | 260/570 |

Primary Examiner—Robert V. Hines
Attorney, Agent, or Firm—Gene Harsh; Joseph C. Gil

[57] ABSTRACT

A process for condensing aromatic amines with formaldehyde in the presence of water is disclosed whereby an inhomogeneous mixture of a reaction product containing a large amount of 4,4'-diamino diphenylmethane is obtained which inhomogenity is due to a large quantity of water which is either present at the beginning of the condensation reaction or which if the reaction is carried out in the presence of relatively small amounts of water is obtained by the subsequent addition of water. The two phases are separated into an organic phase which is directly worked up by distillation without the necessity of an alkaline treatment. The aqueous phase is recycled to the beginning of the process. The process has the advantage of elimination of a salt free effluent, no consumption of acid catalyst and elimination of the need for alkaline reagents.

16 Claims, 1 Drawing Figure

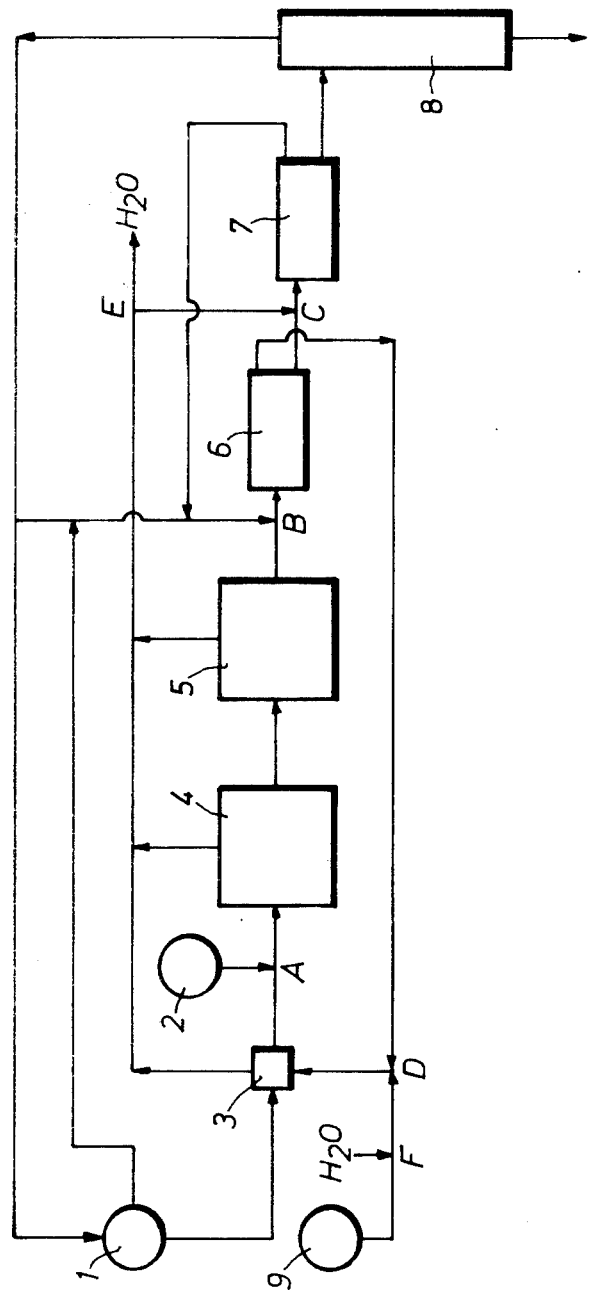

PROCESS FOR THE PRODUCTION OF POLYAMINES

This is a continuation of application Ser. No. 364,187, filed May 25, 1973 and now abandoned.

The production of polyamines of the diamino diphenyl methane series by condensing aromatic amines with formaldehyde in the presence of acid catalysts has frequently been described and gives products differing in their compositions depending upon the procedure adopted. Thus, when condensation is carried out in the presence of weakly acid catalysts or in the presence of traces of strongly acid catalysts, polyamine mixtures with a high proportion of 2,4'-diamino diaryl methanes are obtained. Polyamines with a high proportion of 4,4'-diamino diaryl methanes coupled with a low 2,4'-isomer content can only be produced in the presence of relatively large quantities of strongly acid catalysts. In this particular case, it is best to use strong mineral acids, in particular hydrochloric acid. In conventional processes, however, the advantage of the high selectivity of the strongly acid mineral acids in the formation of 4,4'-isomers can only be obtained at the expense of loss of the catalyst because, on completion of the reaction, the catalyst has to be removed from the reaction mixture by expensive neutralisation with base. Another disadvantage of conventional processes is the fact that the salt solutions accumulating as a result of this neutralisation reaction cannot be put to any valuable commercial use and involve considerable pollution problems.

Accordingly, the object of the invention was to provide a process for the production of higher-nuclear aromatic polyamines by condensing arylamines with formaldehyde in the presence of acid catalysts which does not have any of the disadvantages referred to above.

According to the invention, this object was achieved by carrying out the condensation reaction in the presence of large quantities of water, resulting in the formation of a two-phase reaction product or by adding a further amount of water to the reaction mixture after completion of the reaction in order to provide a two-phase reaction product which in each case contains in the aqueous phase all the acid using as catalyst in the form of the corresponding ammonium salt and contains in the organic phase the required reaction product. Accordingly, by phase separation and recycling the aqueous phase, the acid used as catalyst can be re-used for the condensation reaction. The organic phase containing the reaction product can in turn be worked up by distillation, if desired after it has been washed with water to remove small quantities of dissolved or entrained ammonium salts without the need for any alkaline treatment.

Accordingly, the invention relates to a process for the production of polynuclear aromatic polyamines by condensing aromatic amines with formaldehyde in the presence of water and acid catalysts, wherein a. the reaction is carried out in the presence of such a quantity of water that an inhomogeneous reaction mixture is obtained, or a further amount of water is added to the reaction mixture after the reaction has been completed in order to provide an inhomogeneous reaction mixture, and b. the fully reacted inhomogeneous condensation mixture, if desired following the addition of more of the amine used as starting material, is separated into two phases, of which the organic phase is directly worked up by distillation without any alkaline treatment after washing with water, whilst the aqueous phase is recycled to the beginning of the process.

An apparatus suitable for carrying out the process according to the invention is illustrated by way of example in the accompanying drawing. The principle of the invention is described in the following with reference to this drawing:

A measured, regulated stream of arylamine from the container 1 is combined with the acid aqueous phase from the separator 6 in the mixer 3, and a measured, regulated stream of formaldehyde from the container 2 added to the mixture at point A. The mixture flows into the reactor 4 in which the preliminary reaction takes place, and then into the reactor 5 in which condensation is completed. The aqueous acid condensation mixture then flows into the separator 6 in which the organic phase is separated from the aqueous phase. Water is added to the organic phase containing the polyamines at point C (the water is obtained by evaporation from the reactors 4 or 5 or from the mixer 3 to wash the organic phase. The organic phase is then separated from the washing water in the separator 7 and delivered to the evaporator (8), whose sump product is the polyamine. The arylamine distilling off is returned to the container 1. Some of the amine can be added to the acid condensation mixture at point B in order to improve the separation obtained in the separator 6. The washing water separated off in the separator 7 is also fed in at the same point. The aqueous phase separated off in the separator 6 is recycled to the process by way of the mixer 3. The water introduced, for example with formaldehyde in the form of formalin, and the water of condensation formed is removed by vacuum evaporation in the mixer 3 or in the reactor 4 or by evaporation under normal pressure in the reactor 5, and is discharged from the apparatus at point E. When setting up the process, the apparatus is charged with a given quantity of catalyst from the container 9 at point D. The apparatus can be charged with the necessary quantity of water at the beginning of the process, for example at point F. The temperatures are preferably adjusted as follows: 20° to 60° C in the mixer 3, 20° to 60° C in the reactor (4), 80° to 200° C in the reactor 5 which can be operated under normal pressure or under excess pressure, and 50° to 100° C in the separators 6 and 7.

In the process according to the invention, the quantitative ratios of the reaction components and of the water are selected as follows:

The molar ratio of arylamine to formaldehyde is generally from 50 : 1 to 1 : 1 preferably from 10 : 1 to 1 : 1, more particularly from 4 : 1 to 2 : 1.

The molar ratio of arylamine to catalyst is generally from 20 : 1 to 1 : 1 preferably from 20 : 1 to 2 : 1 more particularly from 10 : 1 to 3 : 1. These ratios are, however, not essential so that higher or smaller ratios may also be applied.

In the process according to the invention, the quantity of water, including both the water which may be used for dissolving the formaldehyde and the water which may be used for dissolving the catalyst added at the beginning of the process, is preferably selected in such a way that a quantity of water corresponding to a ratio by volume of water to arylamine of 10 : 1 to 3 : 1, preferably from 6 : 1 to 3 : 1, is present at the beginning of the process. The molar ratio by volume of water to arylamine at the beginning of the reaction may, however, also be greater than 10 : 1.

Water-soluble acids with a pKa-value of less than 2.5, preferably less than 1.5, are particularly suitable for use in the process according to the invention. Examples of acids such as these include hydrochloric acid, hydrobromic acid, sulphuric acid, trifluoracetic acid, methane sulphonic acid, trifluoromethane sulphonic acid, benzene sulphonic acid or phosphoric acid. Hydrochloric acid is preferably used as the catalyst. The aforementioned acids can also be used in admixture with acid or neutral salts of acids such as these, for example the corresponding ammonium salts or even the corresponding alkali metal salts. The ammonium salts formed from the aforementioned acids and also from the arylamine used as starting amine can of course also be used as sole catalysts right at the beginning of the process.

The following represent particularly suitable aromatic amines for the process according to the invention: aniline, o-toluidine, m-toluidine, N-methylaniline, N-ethylaniline, 2,6-dimethyl aniline, 2,6-diethylaniline, 2,6-diisopropyl aniline, 2,4-diamino toluene, etc., also any mixtures of these amines. Aniline is preferably used as the starting amine in the process according to the invention.

In the process according to the invention, the formaldehyde can also be replaced by any formaldehyde-forming or formaldehyde-yielding substances. However, it is preferred to use an aqueous formalin solution in the process according to the invention.

The condensation mixture used in the process according to the invention can be prepared, for example, by mixing a mixture of arylamine and acid catalyst with formaldehyde or formaldehyde donors and heating the resulting mixture to elevated temperature in order to rearrange the precondensates formed. Conversely, it is also possible initially to react arylamine with formaldehyde and then to add the catalyst to the reaction mixture containing in particular N-substituted intermediate products. The quantity of water present has no bearing upon the acid-catalysed reaction itself. In the extreme case, the condensation reaction can also be carried out in the absence of water. In this case, the water required for phase separation is added to the condensation mixture on completion of the reaction.

The size of the fraction which can be separated off from the acid condensation mixture is governed by the molar ratio of the starting materials, arylamine and catalyst, and is greater, the greater this ratio. In addition, the size of the separable fraction can also be increased by adding more arylamine after the condensation is complete without any change in the arylamine-to-catalyst ratio of the initial reaction mixture. This is particularly advisable when a low arylamine-to-catalyst ratio is used. The quantity is arylamine which may be added during phase separation to reduce the polyamine component recycled in the form of salts can fluctuate within wide limits and generally amounts to between 10 and 500% by weight, preferably to between 50 and 300% by weight, based on the organic components of the condensation mixture.

Water of condensation and water introduced into the system with the starting materials, or which had been previously added to improve the separation of the reaction product previously obtained into two phases, together with solvents (for example methanol from formalin) can be removed from the system at any suitable point, for example at the heating stage in which the condensation reaction is completed, at the precondensation stage which, for this purpose, is carried out under reduced pressure so that the reaction temperature preferably does not exceed 40° to 60° C, or in an evaporator preceding the precondensation stage.

Phase separation of the inhomogeneous condensation mixture is preferably carried out at 80° to 100° C, however, it can also be carried out at lower temperatures such as 0° – 80° C.

The process according to the invention can of course also be carried out completely independently of the apparatus shown purely by way of example in the accompanying drawing. This means in particular that the acid-catalysed amine/formaldehyde condensation can also be carried out in one stage (without the precondensation stage) and either continuously or even in batches. The principle essential to the invention lies in the large quantities of water present in the reaction mixture on completion of the reaction which induces phase separation of the reaction product, in the separation of the end product by simple phase separation and in the re-use of the aqueous phase containing the catalyst in the form of ammonium salts. The quantity of water required for phase separation can be added at the beginning of the process either to the starting materials or even to the condensation product. Generally a ratio by volume of water to organic components of at least 3 : 1 preferably of at least 5 : 1 is necessary to provide a clear separation of the systems into two phases.

Whereas the formaldehyde is generally added to the reaction mixture at the beginning of the condensation reaction the aryl amine may be added at any spot of the cycle. Thus it is, of course, possible, as demonstrated in the drawing to add the aryl amine together with the formaldehyde at the beginning of the condensation. It is, however, for example also possible to carry out the condensation reaction solely with the aryl amine which is recycled in partly or fully protonated form. Since the ammonium salts act as aid to solution for the free amine in water the aqueous phase after phase separation does normally contain a certain amount of free amine. The lower limit of the molar ratio aryl amine/HCl of 1:1 can only be reached if large amounts of water are used and if small amounts of free aryl amine are added prior to the phase separation. A further possibility to add aryl amine to the cycle consists in adding the starting material subsequent to the precondensation step.

The process according to the invention is distinguished in particular by the following advantages:
salt-free effluent
no consumption of acid catalyst
elimination of the need for alkaline reagents.

The invention is illustrated by the following Examples.

EXAMPLE 1

400 ml of 30% aqueous formalin are added at 40° C to a mixture of 800 ml of aniline, 200 ml of 30% aqueous hydrochloric acid and 2500 ml of water. The mixture is brought to the boil and kept under reflux for 3 hours. The organic phase is separated off in a separation funnel, washed with 2 × 200 ml of water and the polyamine freed from volatile constituents by distillation. 439 g of polyamine with the following composition are obtained:

6% of 2,4'-diamino diphenyl methane,
41% of 4,4'-diamino diphenyl methane and
28% of triamines.

The aqueous phase (and washing water) separated off from the organic product still contains 238 g of polyamines and 68 g of aniline together with the catalyst, and is reused in the next batch. For this purpose, 590 ml of water are first distilled off. The remaining solution has 800 ml of aniline and, at 40° C, 400 ml of formalin added to it, followed by heating and further processing as described above. After phase separation of the fully reacted condensation solution and working up, 664 g of polyamine with the following composition are obtained:

5% of 2,4'-diamino diphenyl methane,
49% of 4,4'-diamino diphenyl methane and
24% of triamines.

EXAMPLE 2

The procedure is as in Example 1, except that the quantity of formalin is reduced by half and only 440 ml of water separated off after the first stage. A polyamine of the following composition is obtained (second stage in brackets):

10% (9%) of 2,4'-diamino diphenyl methane,
67% (69%) of 4,4'-diamino diphenyl methane and
12% (11%) of triamines.

EXAMPLE 3

The procedure is as in Example 2, except that the quantity of hydrochloric acid is reduced by half. A polyamine of the following composition is obtained (second stage in brackets):

10% (8%) of 2,4'-diamino diphenyl methane,
63% (65%) of 4,4'-diamino diphenyl methane and
7% (7%) of triamines.

EXAMPLE 4

200 ml of formalin are added at 40° C to a mixture of 400 ml of aniline, 200 ml of hydrochloric acid and, 1250 ml of water. The mixture is brought to the boil and kept under reflux for 1 hour. Following the addition of 800 ml of aniline, the inhomogeneous mixture is separated and the organic phase washed three times with 3 + 200 ml of water. It consists of 516 g of aniline and of 268 g of polyamines with the following composition:

4% of 2,4'-diamino diphenyl methane,
51% of 4,4'-diamino diphenyl methane and
23% of triamines.

The aqueous phase and the washing water contain 314 g of aniline and 83 g of polyamines with the following composition:

3% of 2,4'-diamino diphenyl methane,
84% of 4,4'-diamino diphenyl methane and
12% of triamines.

EXAMPLE 5

The procedure is as in Example 1, except that the aniline is replaced by an equivalent molar quantity of N-methyl aniline. A polyamine of the following composition is obtained (composition of the aqueous phase in brackets):

74% (88%) of diamines,
24% (12%) of triamines.

EXAMPLE 6

This Example illustrates a continuous process (cf. drawing).

A measured, regulated stream of 4 parts by volume of aniline from container 1 is combined with the acid aqueous phase from the separator 6 in the mixer 3 which is kept under a pressure of 50 Torr and which is kept at a temperature of 40° C. The water which evaporates is delivered to the separator 7. 2 parts by volume of 30% aqueous formalin are added at A to the aniline-HCl-water mixture, so that a mixture with an aniline : HCl molar ratio of 4 : 1 and an aniline : formaldehyde molar ratio of 2 : 1 is formed. The quantity of hydrochloric acid present in the system is introduced into the installation at the outset from container 9 at point D and is recirculated. The mixture formed at point A enters the reactor 4 which is evacuated to 50 Torr and whose distillate is combined with that of the mixer 3. The reaction mixture leaving the reactor 4 at a temperature of 40° C enters the heated reactor 5 and then flows into the separator 6 in which it is separated at 90° C. The aqueous phase which separates off is recycled by way of the mixer 3, whilst the organic phase is washed with water which has been distilled off in parts 3 and 4 of the apparatus and which is added at point C, and introduced into the separator 7. The aqueous phase separated in the separator 7 is returned to the separator 6 at point B, whilst the organic phase flows into the distillation column 8 in which excess aniline is separated off from the polyamine and flows back into the container 1. Water is removed at point E in such a quantity that the ratio by volume of water to aniline at the inlet end of the reactor 4 is kept at a value of from 2.5 to 3.0 : 1. The polyamine leaving the column 8 has the following composition:

6% of 2,4'-diamino diphenyl methane,
55% of 4,4'-diamino diphenyl methane and
22% of triamines.

We claim:
1. A process for the preparation of multi-nuclear aromatic polyamines which comprises the steps of
  A. condensing an aromatic amine with formaldehyde in the presence of an aqueous acid catalyst and in the presence of water in a volumetric ratio of water to aromatic amine of at least 3:1, thereby producing an inhomogeneous reaction mixture comprising an aqueous phase containing the acid catalyst as ammonium salts of said aromatic amine, and an organic phase,
  B. recovering polyamine from said organic phase, and
  C. returning said aqueous phase containing the ammonium salt to step (A).
2. The process of claim 1, wherein the condensation reaction is carried out in the presence of quantity of water corresponding to a volumetric ratio of water to aromatic amine of from 3:1 to 10:1.
3. The process of claim 1, wherein following step (A) but before step (B) additional aromatic amine is added in a quantity of from 10 to 500% by weight based on the organic components of the condensation mixture.
4. The process of claim 1, wherein said aromatic amine is selected from the group consisting from aniline, o-toluidine, N-methyl aniline, N-ethyl aniline or mixtures thereof.

5. The process of claim 1, wherein a water soluble acid having a pKa value of less than 2.5 is used as a catalyst.

6. The process of claim 5, wherein the catalyst is hydrochloric acid.

7. The process of claim 1, wherein the molar ratio of aromatic amine to formaldehyde is from 50:1 to 1:1.

8. The process of claim 7, wherein the molar ratio of aromatic amine to acid catalyst is from 20:1 to 1:1.

9. A process for the preparation of multi-nuclear aromatic polyamines which comprises the steps of
   A. condensing an aromatic amine with formaldehyde in the presence of an aqueous acid catalyst,
   B. adding water in a volumetric ratio of water to organic material of at least 3:1, thereby producing an inhomogeneous reaction mixture comprising an aqueous phase containing the acid catalyst as ammonium salts of said aromatic amine, and an organic phase,
   C. recovering polyamine from said organic phase, and
   D. returning said aqueous phase containing the acid ammonium salt catalyst to step (A).

10. The process of claim 9, wherein the condensation reaction is carried out in the presence of quantity of water corresponding to a volumetric ratio of water to aromatic amine of from 3:1 to 10:1.

11. The process of claim 9, wherein following step (A) but before step (B) additional aromatic amine is added in a quantity of from 10 to 500% by weight based on the organic components of the condensation mixture.

12. The process of claim 9, wherein said aromatic amine is selected from the group consisting from aniline, o-toluidine, N-methyl aniline, N-ethyl aniline or mixtures thereof.

13. The process of claim 9, wherein a water soluble acid having a pKa value of less than 2.5 is used as a catalyst.

14. The process of claim 13, wherein the catalyst is hydrochloric acid.

15. The process of claim 9, wherein the molar ratio of aromatic amine to formaldehyde is from 50:1 to 1:1.

16. The process of claim 15, wherein the molar ratio of aromatic amine to acid catalyst is from 20:1 to 1:1.

* * * * *